United States Patent [19]

Gunasekera et al.

[11] Patent Number: 5,073,572
[45] Date of Patent: Dec. 17, 1991

[54] BIOACTIVE METABOLITES FROM *CRIBROCHALINA VASCULUM*

[75] Inventors: Sarath P. Gunasekera, Vero Beach; Glynn T. Faircloth; Amy E. Wright, both of Ft. Pierce; Winnie C. Thompson, Vero Beach, all of Fla.; Neal Burres, Highland Park, Ill.

[73] Assignee: Harbor Branch Oceanographic Institution, Inc., Fort Pierce, Fla.

[21] Appl. No.: 481,475

[22] Filed: Feb. 16, 1990

[51] Int. Cl.$^5$ .................... C07C 33/02; C07C 33/03; A61K 31/045; A61K 31/22

[52] U.S. Cl. .................... 514/739; 514/544; 514/546; 514/552; 560/113; 560/261; 568/873

[58] Field of Search ............... 568/873; 560/113, 261; 514/739, 544, 546, 552

[56] References Cited

U.S. PATENT DOCUMENTS

| | | | |
|---|---|---|---|
| 2,865,967 | 12/1958 | Barley et al. | 568/873 |
| 3,379,777 | 4/1968 | Marlet | 568/873 |
| 4,026,960 | 5/1977 | Nishida et al. | 568/873 |
| 4,548,814 | 10/1985 | Rinehart, Jr. | 424/95 |
| 4,729,996 | 3/1988 | Wright et al. | 514/215 |
| 4,737,510 | 4/1988 | Rinehart, Jr. | 514/388 |
| 4,808,590 | 2/1989 | Higa et al. | 514/272 |
| 4,916,160 | 4/1990 | Morita et al. | 514/546 |
| 4,935,439 | 6/1990 | Kashman et al. | 514/546 |
| 5,004,735 | 4/1991 | Okamoto et al. | 514/739 |

FOREIGN PATENT DOCUMENTS

| | | | |
|---|---|---|---|
| 46808 | 4/1981 | Japan | 514/552 |
| 696235 | 8/1953 | United Kingdom | 568/873 |

OTHER PUBLICATIONS

Cimino, G., A. Crispino, S. De Rosa, S. De Stefano, G. Sodano (1981) "Polyacetylenes from the Sponge *Petrosia ficiformis* found in dark caves," Experientia 37:924–926.

Fusetani, N., Y. Kato, S. Matsunaga, K. Hashimoto (1983) "Bioactive Marine Metabolites III. A Novel Polyacetylene Alcohol, Inhibitor of Cell Division in Fertilized Sea Urchin Eggs, from the Marine Sponge Tetrosia sp.," Tetrahedron Letters 24(27):2771–2774.

Wright, A. E., O. J. McConnell, S. Kohmoto, M. S. Lui, W. Thompson, K. M. Snader (1987) "Duryne, a New Cytotoxic Agent From the Marine Sponge *Cribrochalina dura*," Tetrahedron Letters 28(13):1377–1380.

Castiello, D., G. Cimino, S. De Rosa, S. De Stefano, G. Sodano (1980) "High Molecular Weight Polyacetylenes from the Nudibranch *Peltodoris atromaculata* and the Sponge *Petrosia ficiformis*," Tetrahedron Letters 21:5047–5050.

Cimino, G., A. De Guilio, S. De Rosa, B. De Stefano, G. Sodano (1985) "Further High Molecular Weight Polyacetylenes from the Sponge *Petrosia ficiformis*," J. Natural Products 48(1):22–27.

Quinoa, E., P. Crews (1988) "Melynes, Polyacetylene Constituents from a Vanatu Marine Sponge," Tetrahedron Letters 29(17):2037–2040.

Rotenm, M., Y. Kashman (1979) "New Polyacetylenes from the Sponge Siphonochalina sp.," Tetrahedron Letters 34:3193–3196.

Fusetani, N., M. Sugano, S. Matsunaga, K. Hashimoto (1987) "H,K-ATPase Inhibitors from the Marine Sponge *Siphonochalina truncats*: Absolute Configuration of Siphonodiol and Two Related Metabolites," Tetrahedron Letters 28(37):4311–4312.

Hansen, L., P.M. Boli (1986) "Polyacetylenes in Araliaceae: Their Chemistry, Biosynthesis and Biological Significance," Phytochemistry 25(2):285–293.

*Primary Examiner*—J. E. Evans
*Attorney, Agent, or Firm*—Saliwanchik & Saliwanchik

[57] ABSTRACT

Novel acetylenic alcohols were isolated from the known marine sponge *Cribrochalina vasculum*. These compounds, and derivatives thereof, are useful agents for the treatment of cancers of humans and animals. Also, these compounds and their derivatives can be used as immunosuppressive agents for humans and animals.

21 Claims, No Drawings

BIOACTIVE METABOLITES FROM *CRIBROCHALINA VASCULUM*

BACKGROUND OF THE INVENTION

Marine life has been the source for the discovery of compounds having varied biological activities. Some of the U.S. patents which have issued for such inventions are as follows: U.S. Pat. No. 4,548,814 for didemnins, having antiviral activity, were isolated from a marine tunicate; U.S. Pat. No. 4,729,996 discloses compounds, having antitumor properties, that were isolated from marine sponges *Teichaxinella morchella* and *Ptilocaulis walpersi*; U.S. Pat. No. 4,808,590 discloses compounds, having antiviral, antitumor and antifungal properties, isolated from the marine sponge Theonella sp.; and, U.S. Pat. No. 4,737,510 discloses compounds, having antiviral and antibacterial properties, isolated from the Caribbean sponge *Agelas coniferin*. Though marine life has been the source of useful chemicals, there remains a need to discover more compounds which can be used medically to treat a wide range of diseases afflicting animals and humans.

The subject invention concerns novel acetylenic alcohols isolated from the known marine sponge *Cribrochalina vasculum*. Several classes of noncyclic acetylenic compounds have been isolated from terrestrial plants as well as from marine organisms. Most of these compounds fall into the basic category referred to as the polyacetylenic compounds, having more than one acetylenic moieties. Several groups have reported the isolation of these polyacetylenic compounds from marine organisms. The acetylenic carbinols identified to date have been shown to contain more than one acetylenic carbinol moieties. See the following publications:

- Cimino, G., A. Crispino, S. De Rosa, S. De Stefano and G. Sodano (1981) "Polyacetylenes from the sponge *Petrosia ficiformis* found in dark caves," Experientia 37:924–926.
- Fusetani, N., Y. Kato, S. Matsunaga and K. Hashimoto (1983) "Bioactive marine metabolites III. A novel polyacetylene alcohol, inhibitor of cell division in fertilized sea urchin eggs, from the marine sponge Tetrosia sp.," Tetrahedron Letters, 24 (27):2771–2774.
- Wright, A. E., O. J. McConnell, S. Kohmoto, M. S. Lui, W. Thompson and K. M. Snader (1987) "Duryne, a new cytotoxic agent from the marine sponge *Cribrochalina dura*," Tetrahedron Letters, 28 (13):1377–1380
- Castiello, D., G. Cimino, S. De Rosa, B. De Stefano and G. Sodano (1980) "High molecular weight polyacetylenes from the nudibranch *Peltodoris atromaculata* and the sponge *Petrosia ficiformis*," Tetrahedron Letters 21:5047–5050
- Cimino, G., A. DeGiulio, S. De Rosa, S. De Stefano and G. Sodano (1985) "Further high molecular weight polyacetylenes from the sponge *Petrosia ficiformis*," J. Natural Products, Vol. 48, 1:22–27
- Quinoa, E. and P. Crews (1988) "Melynes, polyacetylene constituents from a Vanuatu sponge," Tetrahedron Letters, 29 (17):2037–2040
- Rotem, M. and Y. Kashman (1979) "New polyacetylenes from the sponge Siphonochalina sp.," Tetrahedron Letters 34:3193–3106
- Fusetani, N., M. Sugano, S. Matsunaga and K. Hashimoto (1987) "H,K-ATPase inhibitors from the marine sponge *Siphonochalina truncata*: Absolute configuration of siphonodiol and two related metabolites," Tetrahedron Letters, 28 (37):4311–4312
- Hansen, L. and P. M. Boll (1986) "Polyacetylenes in Araliaceae: Their chemistry, biosynthesis and biological significance," Phytochemistry, 25 (2):285–293

The compounds of the subject invention are clearly different from the prior art as follows:

(1) The invention compounds are non-cyclic monoacetylenic carbinols;

(2) These invention compounds are the first report of branched acetylenes of this nature isolated from a natural source;

(3) The invention compounds are unique in having a single terminal 3-ol, 4-en, 1-yne moiety attached to an alkyl chain; and, (4) These invention compounds are the first report of such acetylenic compounds known to possess immunosuppressive activities.

BRIEF SUMMARY OF THE INVENTION

The subject invention concerns novel acetylenic compounds isolated from the marine sponge *Cribrochalina vasculum*. These compounds, and derivatives thereof, can be shown by the following generic structure:

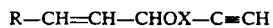

$$R-CH=CH-CHOX-C\equiv CH$$

wherein R is selected from the group consisting of:
—$(CH_2)_{14}CH_3$; (Compound 1)
—$(CH_2)_9CH=CH-(CH_2)_5-CH_3$; (Compound 2)
—$(CH_2)_{10}-CH(CH_3)_3-(CH_2)-CH_3$; (Compound 3)
—$(CH_2)_{13}-CH(CH_3)_2$; (Compound 4) and,
—$(CH_2)_9-CH=CH-(CH_2)_4CH(CH_3)_2$; (Compound 5)

wherein X is selected from the group consisting of H, $COR_1$, and benzoyl, wherein $R_1$ is selected from the group consisting of —$CH_3$, and —$(CH_2)_nCH_3$, wherein n is an integer from 1–10.

The parent compounds (5 compounds) have the structures wherein R is as given, and X is H. The subject invention also includes the acetates, and benzoates of the above compounds. There derivatives can be prepared according to well known procedures. The parent compounds can be isolated from the pertinent marine sponge as described in Example 1.

The compounds of the invention, including derivatives thereof, have antitumor and immunosuppressive properties. Thus, they can be used for the inhibition of growth of tumor cells, e.g., leukemia cells or solid tumors. More specifically, the novel compounds of the invention can be used for immunosuppression of humans undergoing transplantation of foreign organs or tissues (bone marrow); treatment of autoimmune diseases; and as chemotherapeutic agents for treatment of animal and human cancers.

When used as immunosuppressive agents, the compounds can be used to treat humans and animals with various diseases. For example, they can be used in diseases such as systemic lupus erythematosus, rheumatoid arthritis, scleroderma, dermatomyositis, polymyositis, unclassified connective tissue diseases, autoimmune hemolytic anemia, idiopathic thrombocytopenic purpura, autoimmune thyroiditis, polyarteritis nodosum, glomerulonephritis, uveitis, etc, to prevent the rejection of organ allografts or to alleviate some of the pathological effects of autoimmunity.

DETAILED DISCLOSURE OF THE INVENTION

The compounds of the invention were isolated from the known marine sponge *C. vasculum*. The sponge was collected using scuba techniques at Northeast Glover's Reef (16 50' N, 87 43' W), Belize at a depth of approximately 40 feet.

*C. vasculum* is classified as follows:
Phylum Porifera
Class Demospongia
Order Haplosclerida
Family Niphatidae The *C. vasculum* sample from which the novel compounds of the invention were isolated has the following characteristics:

Sample 20-XI-58-2-13: vase-shaped sponge, approximately 25 cm high, 20 cm diameter at apex, 5 cm diameter at base; color purplish brown externally, cream internally; in ethanol, the sponge is tan; surface smooth, but covered with white zooanthids; consistency firm, tough; spicules oxeas, skeletal arrangement as described by Weidenmayer, F. (1977) Experientia Supp. 28, 287 pp. and Soest, R. W. M. van (1980) Stud. Fauna Curacao and Other Caribb. Islands, Vol. 62, 104:1–174. IRCZM catalog #:003:0038 (voucher deposited at Indian River Coastal Zone Museum, Harbor Branch Oceanographic Institute (HBOI).

The compounds of the invention are useful for various non-therapeutic and therapeutic purposes. For example, they can be used as ultraviolet screeners in the plastics industry since they effectively absorb UV rays. As disclosed herein, they are also useful prophylactically and therapeutically for treating tumors in animals and humans. Further, the novel compounds can be used to treat animals and humans in need of immunosuppression.

The dosage administration to a host in the above indications will be dependent upon the identity of the tumor invasion, the type of host involved, its age, health, weight, kind of concurrent treatment, if any, frequency of treatment and therapeutic ratio. Dosage administration when used as immunosuppressive agents will be dependent on the disease and the other conditions as stated above.

Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Expressed in terms of concentration, an active ingredient can be present in the compositions of the present invention for localized use about the cutis, intranasally, pharyngolayngeally, bronchially, intravaginally, rectally, or ocularly in a concentration of from about 0.01 to about 50% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile non-parenteral solutions of suspensions, and oral solutions or suspensions, and the like, containing quantities of an active ingredient.

Suitable formulations of the compounds can be made as disclosed in U.S. Pat. No. 4,737,510 by substituting the novel compounds of this invention for the halopyrrole of U.S. Pat. No. 4,737,510.

Following are examples which illustrate procedures, including the best mode, for practicing the invention. These examples should not be construed as limiting. All percentages are by weight and all solvent mixture proportions are by volume unless otherwise noted.

EXAMPLE 1—EXTRACTION AND ISOLATION PROCEDURES

The marine sponge *Cribrochalina vasculum* (20-IX-85-2-13) was collected at Glover Reef, Belize, at a depth of approximately 40 feet. The freshly thawed sponge (197 g, wet wt.) was extracted twice with a mixture of MeOH and 25% toluene. The concentrated extract was then partitioned between EtOAc and $H_2O$. The immunosuppressive, EtOAc soluble fraction (128 mg) was chromatographed over $SiO_2$ gel [Kieselgel 60H] and monitored by immunomodulatory assay. The immunosuppressive active fraction (33 mg) was further separated by reverse phase HPLC (5 micron, C-18, 7% $H_2O$-MeOH) to yield 15 related compounds, of which 5 compounds showed immunosuppressive activity in the two-way mixed lymphocyte reaction (MLR). The active compounds were further purified by reverse phase HPLC to give five essentially pure compounds 1–5.

Other solvents which can be used in the extraction are heptane, hexane, acetone, methanol, ethanol, isopropanol, toluene, chloroform, dichloromethane, diethylether, or any combination of these solvents.

The UV spectrum was obtained with a Perkin Elmer Lambda 3B UV/Visible spectrometer. Infrared spectrum was determined on a Perkin Elmer 1310 spectrometer. The $^1$H-NMR spectra were recorded on a Brucker 360 MHz instrument. The $^{13}$C-NMR spectra were obtained on the same instrument operated at 90.5 MHz. The high resolution EI mass spectra were obtained with a Finnigan-MAT CH5 spectrometer operating at 70 eV. Optical rotation was measured with a Jasco DIP-360 digital polarimeter.

Compound 1 (SP10098)

0.8 mg; colorless gum; $(\alpha)^{25}D = 3.8°$ (c = 0.9, MeOH); UV $\lambda$ max (MeOH) 202 nm ($\epsilon$ = 1400); IR (CHCl$_3$) 3590, 3295, 2890, 2848, 1000 and 930 cm$^1$; $^1$H NMR (CDCl$_3$) $\delta$0.85 (3H, t, J=6.5 Hz, 21-H), 1.33–1.39 (28H, m, 7-20-H), 2.04 (2H, dt, J=7.0, 6,7 Hz, 6-H), 2.54 (1H, d, J=2.0 Hz, 1-H), 4.81 (1H, ddd, J=6.2, 2.0, 1.2 Hz, 3-H), 5.59 (1H, ddt, J=15.3, 6.1, 1.6 Hz, 4-H). 5.89 (1H, ddt, J=15.3, 6.7 1.4 Hz, 5-H); $^{13}$C NMR (CDCl$_3$), $\delta$14.10 (C, q), 22.68 (C, t), 28.81 (C, t), 29.17 (C, t), 29.36 (C, t), 29.45 (C, t), 29.57 (C, t), 29.67 (7C, t), 31.93 (C, t), 62.81 (C, d), 73.93 (C, d), 83.34 (C, s), 128.31 (C, d), 134.62 (C, d); HREIMS: m/z 292.27573, $\Delta$0.9 mmu for $C_{20}H_{36}O$; LRFDMS: m/z (relative intensity) 292 (60%), 275 (100), 267 (33), 197 (5), 190 (6), 132 (8).

The structure of SP10098 has been determined to be as follows:

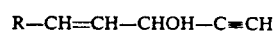

wherein $R = (CH_2)_{14}CH_3$.

Compound 2 (SP10099)

3.7 mg; colorless gum; $(\alpha)^{25}$ D=4.9° (c=4.5, MeOH); UV λ max (MeOH) 204 nm (ε=1400); IR (CHCl$_3$) 3590, 3290, 2895, 2840, 1075, 998 and 965 cm$^{-1}$; $^1$H NMR (CDCl$_3$) δ0.85 (3H, t, J=6.5 Hz, 22-H), 1.20-1.39 (22H, CH$_2$ groups), 1.88 (1H, d, J=5.7 Hz, 3-OH), 2.01 (6H, m, 6, 17, 20-CH$_2$), 2.54 (1H, d, J=2.0 Hz, 1-H), 4.81 (1H, ddd, J=6.0, 5.7, 2.0 Hz, 3-H), 5.32 (2H, m, 18, 19-H), 5.85 (1H, ddt, J=15.3, 6.0, 1.1 Hz, 4-H), 5.89 (1H, ddd, J=15.3, 6.7, 0.9 Hz, 5-H); $^{13}$C NMR (CDCl$_3$), δ14.07 (C, q), 22.62 (C, t), 27.19 (2C, t), 28.81 (C, t), 28.96 (C, t), 29.16 (C, t), 29.27 (C, t), 29.42 (C, t), 29.51 (2C, t), 29.73 (2C, t), 31.75 (C, t), 31.90 (C, t), 62.78 (C, d), 73.90 (C, d), 83.34 (C, s), 128.35 (C, d), 129.85 (C, d), 129.91 (C, d), 134.56 (C, d); HRFABMS: m/z 319.30030, Δ0.2 mmu for C$_{22}$H$_{39}$O, (M++1); LRFDMS: m/z 318 (27), 301 (100), 300 (90), 292 (24), 200 (9), 150 (21).

The structure of SP10099 has been determined to be as follows:

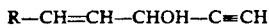

wherein R=(CH$_2$)$_9$—CH=CH—(CH$_2$)$_5$—CH$_3$.

Compound 3 (SP10100)

3.3 mg; colorless gum; $(\alpha)^{25}$D=1.4° (c=5.6, MeOH); UV λ max (MeOH) 205 nm (ε=1400); IR (CHCl$_3$) 3575, 3290, 2840, 1075, 995 and 965 cm$^{-1}$; $^1$H NMR (CDCl$_3$) δ0.81 (3H, d, J=6.4 Hz, 21-H), 0.86 (3H, d, J=6.5 Hz, 20-H), 1.04 (2H, m, CH$_2$), 1.2-1.4 (25H, m, CH and CH$_2$ groups), 1.84 (1H, d, J=3.5 Hz, 3-OH), 2.04 (2H, dt, J=7.1, 6.8 Hz, 6-H), 2.53 (1H, d, J=2.0 Hz, 1-H), 4.81 (1H, ddd, J=6.1, 3.5, 2.0 Hz, 3-H), 5.58 (1H, ddt, J=15.3, 6.1, 1.0 Hz, 4-H), 5.89 (1H, ddt, J=15.3, 6.7, 0.9 Hz, 5-H); $^{13}$C NMR (CDCl$_3$), δ14.09 (C, q), 19.68 (C, q), 22.67 (C, t), 27.04 (C, t), 28.81 (C, t), 29.17 (C, t), 29.37 (C, t), 29.48 (C, t), 29.59 (C, t), 29.67 (C, t), 29.90 (C, t), 29.97 (C, t), 31.93 (C, t), 32.72 (C, d), 37.06 (C, t), 37.07 (C, t), 62.75 (C, d), 73.90 (C, d), 83.34 (C, s), 128.35 (C, d), 134.54 (C, d); HRFABMS m/z 307.30080, Δ0.7 mmu for C$_{21}$H$_{39}$O, (M++1); LRFDMS: m/z 306 (55), 289 (95), 287 (38), 281 (22), 280 (22), 153 (10), 85 (32), 84 (100).

The structure of SP10100 has been determined to be as follows:

R—CH=CH—CHOH—C≡CH wherein R=(CH$_2$)$_{10}$—CH(CH$_3$)(CH$_2$)$_3$—CH$_3$.

Compound 4 (SP10101)

2.2 mg; colorless gum; $(\alpha)^{25}$D=2.6° (c=1.0, MeOH); UV λ max (MeOH) 204 nm (ε=1400); IR (Neat) 3270, 2922, 2858, 1467, 1012 and 970 cm$^{-1}$; $^1$H NMR (CDCl$_3$) δ0.84 (6H, d, J=6.7 Hza, 20, 21-H), 1.10-1.34 (25H, m, 7-19H), 1.76 (1H, d, J=6.1 Hz, 3-OH), 2.04 (2H, dt, J=7.1, 6.8 Hz, 6-H), 2.54 (1H, d, J=2.0 Hz, 1-H), 4.81 (1H, ddd, J=6.1, 3.5, 2.0 Hz. 3-H), 5.58 (1H, ddt, J=15.3, 6.0, 1.1 Hz, 4-H), 5.90 (1H, ddt, J=15.3, 6.7, 0.9 Hz, 5-H); $^{13}$C NMR (CDCl$_3$), δ22.65 (2C, q), 27.09 (C, t), 27.39 (C, t), 27.95 (C, d), 28.81 (C, t), 29.17 (C, t), 29.45 (C, t), 29.57 (C, t), 29.66 (5C, t), 29.92 (C, t), 30.00 (C, t), 31.90 (C, t), 39.04 (C, t), 62.78 (C, d), 73.90 (C, d), 83.34 (C, s); HREIMS m/z 306.29147, Δ0.8 mmu for C$_{21}$H$_{38}$O; LRFDMS: m/z 306 (100), 291 (27), 288 (22), 280 (30), 277 (32), 263 (65).

The structure of SP10101 has been determined to be as follows:

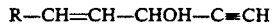

wherein R=(CH$_2$)$_{13}$—CH(CH$_3$)$_2$.

Compound 5 (SP10102)

1.7 mg; colorless gum; $(\alpha)^{25}$ D=2.0° (c=0.01, MeOH); UV λ max (MeOH) 204 nm (ε=1500); IR (Neat) 3318, 2930, 2860, 1465, 1010 and 968 cm$^{-1}$; $^1$H NMR (CDCl$_3$) δ0.84 (6H, d, J=6.3 Hz, 22, 23-H), 1.14-1.39 (21H, m, 7-13 and 18-21-H), 1.82 (1H, d, J=5.3 Hz, 3-OH), 2.03 (6H, m, 6, 14, 17-H), 2.54 (1H, d, J=2.0 Hz, 1-H), 4.81 (1H, ddd, J=5.3, 3.5, 2.0 Hz, 3-H), 5.32 (2H, m, 15, 16-H), 5.58 (1H, ddt, J=15.0, 6.1, 1.6 Hz, 4-H), 5.89 (1H, ddt, J=15.0, 6.7, 0.9 Hz, 5-H); $^{13}$C NMR (CDCl$_3$), δ22.62 (2C, q), 27.06 (C, t), 27.19 (C, q), 27.95 (C, d), 28.80 (C, t), 29.17 (C, t), 29.27 (C, t), 29.44 (2C, t), 29.51 (C, t), 29.66 (C, t), 29.75 (C, t), 30.00 (C, t), 31.91 (C, t), 38.88 (C, t), 62,79 (C, d), 73.92 (C, d), 83.24 (C, s), 128.34 (C, d), 129.87 (2C, d), 134.59 (C, d); HREIMS m/z 332.30713, Δ0.8 mmu for C$_{23}$H$_{40}$O; LRFDMS: m/z 332 (44), 315 (100), 314 (84), 307 (9), 306 (13).

The structure of SP10102 has been determined to be as follows:

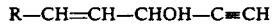

wherein R=(CH$_2$)$_9$—CH=CH—(CH$_2$)$_4$CH(CH$_3$)$_2$.

METHODS FOR BIOLOGICAL TESTING

Immunomodulator Methodology

The crude ethanolic extract was tested in the two-way mixed lymphocyte reaction (MLR) and a CV-1 cytotoxicity assay at a 1X concentration of the crude extract, using murine splenocytes. Cellular proliferation was measured using incorporation of $^3$H-thymidine.

The pure compounds were tested for immunosuppressive effects in the MLR assay and for specific cytotoxicity effects in the lymphocyte viability (LCV) assay both using murine splenocytes. Cellular proliferation was determined using incorporation of $^3$H-thymidine and a modified form of the M. T. T. assay (Mosmann, T. [1983] "Rapid colorimetric assay for cellular growth and survival: Application to proliferation and cytotoxicity assays," J. Immunol. Methods, 65:55-63). Responses were reported as a percent of the positive MLR or LCV control. As a general rule, a low MLR value combined with a high LCV value indicates immunosuppressive activity. Specifically, a value of less than 10% of the positive control MLR with a corresponding LCV value of greater than 60% suggests optimal immunosuppressive effects of the compound.

Antitumor Methodology

The crude ethanolic extract and essentially pure compound were tested for toxicity against murine P388 leukemia cells and cells derived from human colon (HT-29) and lung (A549) tumors. P388 cells obtained from Dr. J. Mayo, National Cancer Institute, Bethesda Md., were maintained in Roswell Park Memorial Institute (RPMI) medium 1640 supplemented with 10% horse serum. HT-29 and A-459 human tumor cells were obtained from the American Type Culture Collection (Rockville, Md.) and maintained in RPMI medium 1640 supplemented with 10% fetal bovine serum. All cell lines were cultured in plastic tissue culture flasks and kept in an incubator at 37° C. in humidified air containing 5% $CO_2$. Antibiotic-free stock cultures of P388 cells were subcultured to $10^5$ cells/ml by dilution in fresh growth medium at 2 to 3 day intervals. The mean generation time of primary P388 cultures was 14 to 17 hr. HT-29 and A549 cells were subcultured after dissociation with trypsin-EDTA at weekly intervals.

To assess the antiproliferative effects of agents against P388, HT-29, and A549 cells, 200 μl cultures (96-well tissue culture plates, Nunc, Denmark) were established at $1 \times 10^5$ cells/ml (4000 cells/cm² for HT-29 and A549) in drug-free medium or medium containing the crude extract at a final dilution of 1:500 of test compound at various concentrations. Solvent for all dilutions was methanol, which was removed from plates under vacuum. All experimental cultures were initiated in medium containing Gentamicin sulfate (50 mg/ml; Schering Corporation, Kenilworth, N.J.). After 48-h exposures, P388 cells were enumerated using 3-[4,5-Dimethylthiazol-2-yl]-2,5-diphenyltetrazolium bromide (MTT) as described below (Alley, M. C., et al.[1988] Cancer Res. 48:589).

To quantitate the effects on cell proliferation, 75 μl of warm growth medium containing 5 mg/ml MTT was added to each well and cultures were returned to the incubator for 90 minutes. To spectrophotometrically quantitate MTT, plates were centrifuged (900×g, 5 minutes), culture fluids removed by aspiration, and 200 μl of acidified isopropanol (2 ml concentrated HCl/liter isopropanol) added per well. The absorbance of the resulting solutions were measured at 570 nm with a plate reader (MR700 Microplate Reader, Dynatech, Laboratories, Chantilly, Va.). The absorbance of test wells was divided by the absorbance of drug-free wells, and the concentration of agent that resulted in 50% of the absorbance of untreated cultures was determined by linear regression of logit-transformed data (Finney, D. J., [1978] Statistical Method in Biological Assay, third ed. pp. 316-348. Charles Griffin Co., London). A linear relationship between tumor cell number and formazan produced was found over the range of cell densities observed in these experiments.

EXAMPLE 2—IMMUNOSUPPRESSIVE ACTIVITY TESTING OF NOVEL COMPOUNDS (A) Crude Extract of Sample 20-XI-85-2-13

| Dilution | $^a$MLR % | $^b$CV-1 Toxicity |
|---|---|---|
| 1X (10 μl) | ≦1 | 0 |

(B) Essentially Pure Compounds

| Compound | Dose ug/well | $^a$MLR % | $^b$LCV % |
|---|---|---|---|
| SP10098 | 10. | 0 | 2 |
| (9SG 52-3) | 1. | 0 | 21 |
| | 0.1 | 0 | 61 |
| | 0.01 | 24 | 80 |
| SP10099 | 10. | 0 | 22 |
| (9SG 52-4) | 1. | 0 | 13 |
| | 0.1 | 0 | 34 |
| | 0.01 | 33 | 67 |
| SP10100 | 10. | 0 | 8 |
| (9SG 52-5) | 1. | 0 | 12 |
| | 0.1 | 0 | 42 |
| | 0.01 | 21 | 78 |
| SP10101 | 10. | 0 | 10 |
| (9SG 52-6) | 1. | 0 | 7 |
| | 0.1 | 0 | 49 |
| | 0.01 | 21 | 82 |
| SP10102 | 10. | 0 | 0 |
| (9SG 52-7) | 1. | 0 | 15 |
| | 0.1 | 0 | 45 |
| | 0.01 | 20 | 67 |

$^a$Two-way murine mixed lymphocyte response. Results are expressed as a percentage of the positive MLR control response (no compound).
$^b$Viability (LCV) of lymphocytes as measured by metabolism of M.T.T. Results are expressed as a percentage of the positive LCV control response (no compound).

EXAMPLE 3—CYTOTOXIC ACTIVITY TESTING OF THE NOVEL COMPOUNDS (A) Essentially Pure Compounds SP10098 through SP10102 inhibit the proliferation of murine P388 leukemia cells, and cells derived from human lung (A549) and colon (HT-29) tumors.

| ID of sample submitted | Compound | $IC_{50}S^*$ μg/ml P388 | A549 | HT-29 |
|---|---|---|---|---|
| 9SG 53-1 | SP10098 | 1.21 ± 0.73(4) | 1.60 ± 0.10(3) | 1.66 ± 0.47(3) |
| 9SG 55-1 | SP10099 | 1.23 ± 0.53(3) | 1.75 ± 0.06(4) | 1.66 ± 0.15(3) |
| 9SG 56-1 | SP10100 | 1.58 ± 0.51(3) | 1.56 ± 0.06(3) | 0.86 ± 0.06(3) |
| 9SG 62-2 | SP10101 | 1.44 ± 0.28(4) | 2.30 ± 0.70(3) | 1.06 ± 0.11(3) |
| 9SG 63-2 | SP10102 | 1.63 ± 0.29(4) | 2.90 ± 0.34(3) | 1.46 ± 0.06(3) |

*mean ± S.D., n = (190) separate determinations

We claim:

1. A compound, essentially pure, which can be shown by the following structure:

R—CH=CH—CHOX—C≡CH wherein R is selected from the group consisting of:
—$(CH_2)_{14}CH_3$;
—$(CH_2)_9CH=CH—(CH_2)_5—CH_3$;
—$(CH_2)_{10}—CH(CH_3)—(CH_2)_3—CH_3$;
—$(CH_2)_{13}—CH(CH_3)_2$; and,
—$(CH_2)_9—CH=CH—(CH_2)_4CH(CH_3)_2$;
wherein X is selected from the group consisting of H, $COR_1$, and benzoyl, wherein $R_1$ is selected from the group consisting of —$CH_3$, and —$(CH_2)_nCH_3$, wherein n is an integer from 1-10.

2. The compound, according to claim 1, wherein R is —$(CH_2)_{14}CH_3$, and X is H.

3. The compound, according to claim 1, wherein R is —$(CH_2)_9CH=CH—(CH_2)_5—CH_3$, and X is H.

4. The compound, according to claim 1, wherein R is —$(CH_2)_{10}—CH(CH_3)—(CH_2)_3—CH_3$, and X is H.

5. The compound, according to claim 1, wherein R is —$(CH_2)_{13}—CH(CH_3)_2$, and X is H.

6. The compound, according to claim 1, wherein R is —$(CH_2)_9—CH=CH—(CH_2)_4CH(CH_3)_2$, and X is H.

7. A process for inhibiting the growth of tumor or cancer cells which comprises administering an effective amount of a compound of claim 1.

8. A process, according to claim 7, for inhibiting the growth of tumor or cancer cells wherein R is selected from the group consisting of:
- —$(CH_2)_{14}CH_3$;
- —$(CH_2)_9CH=CH-(CH_2)_5-CH_3$;
- —$(CH_2)_{10}-CH(CH_3)_3-(CH_2)-CH_3$;
- —$(CH_2)_{13}-CH(CH_3)_2$; and,
- —$(CH_2)_9-CH=CH-(CH_2)_4CH(CH_3)_2$;

and wherein X is H.

9. The process, according to claim 7, wherein R is —$(CH_2)_{14}CH_3$, and X is H.

10. The process, according to claim 7, wherein R is —$(CH_2)_9CH=CH-(CH_2)_5-CH_3$, and X is H.

11. The process, according to claim 7, wherein R is —$(CH_2)_{10}-CH(CH_3)-(CH_2)_3-CH_3$, and X is H.

12. The process, according to claim 7, wherein R is —$(CH_2)_{13}-CH(CH_3)_2$, and X is H.

13. The process, according to claim 7, wherein R is —$(CH_2)_9-CH=CH-(CH_2)_4CH(CH_3)_2$, and X is H.

14. The process, according to claim 7, wherein said cells are selected from the group consisting of solid tumor cells and leukemia cells.

15. A process for treating a human or animal in need of immunosuppression which comprises administering to said human or animal an effective immunosuppressive amount of a compound of claim 1.

16. A process, according to claim 15, wherein R is selected from the group consisting of:
- —$(CH_2)_{14}CH_3$;
- —$(CH_2)_9CH=CH-(CH_2)_5-CH_3$;
- —$(CH_2)_{10}-CH(CH_3)-(CH_2)_3-CH_3$;
- —$(CH_2)_{13}-CH(CH_3)_2$; and,
- —$(CH_2)_9-CH=CH-(CH_2)_4CH(CH_3)_2$;

and wherein X is H.

17. The process, according to claim 15, wherein R is —$(CH_2)_{14}CH_3$, and X is H.

18. The process, according to claim 15, wherein R is —$(CH_2)_9CH=CH-(CH_2)_5-CH_3$, and X is H.

19. The process, according to claim 15, wherein R is —$(CH_2)_{10}-CH(CH_3)-(CH_2)_3-CH_3$, and X is H.

20. The process, according to claim 15, wherein R is —$(CH_2)_{13}-CH(CH_3)_2$, and X is H.

21. The process, according to claim 15, wherein R is —$(CH_2)_9-CH=CH-(CH_2)_4CH(CH_3)_2$, and X is H.

* * * * *

UNITED STATES PATENT AND TRADEMARK OFFICE
CERTIFICATE OF CORRECTION

PATENT NO.    : 5,073,572

DATED         : December 17, 1991

INVENTOR(S)   : Sarath P. Gunasekera, Glynn T. Faircloth, Any E. Wright, Winnie C. Thompson, Neal Burres It is certified that error appears in the above-identified patent and that said Letters Patent is hereby corrected as shown below:

Column 5: Line 60: "$H_2$. 3-H" should read --$H_2$, 3-H--.".

Column 7: Line 62: Lines omitted should read --[a] Two-way mixed lymphocyte response. Results are expressed as a percentage of the positive MLR control response (no compound).
[b] Toxicity determined using the CV-1 cell line. Results are expressed as a zone in millimeters of dead cells (0 mm = no cytotoxicity, 16 mm = maximum cytotoxicity).--

Column 7: line 39: "n = (190)" should read --n = (#)--.

Signed and Sealed this

Eighteenth Day of May, 1993

*Attest:*

MICHAEL K. KIRK

*Attesting Officer*    Acting Commissioner of Patents and Trademarks